United States Patent [19]

Marttila et al.

[11] Patent Number: 4,935,247
[45] Date of Patent: Jun. 19, 1990

[54] COMPOSITION FOR THE ORAL ADMINISTRATION OF PHARMACEUTICALS

[75] Inventors: Esko Marttila, Perttula; Ilkka Larma, Espoo; Kari Vahervuo, Espoo; Jaakko Uotila, Espoo, all of Finland

[73] Assignee: Orion-Yhtymä Oy, Finland

[21] Appl. No.: 191,190

[22] Filed: May 6, 1988

[30] Foreign Application Priority Data

May 8, 1987 [FI] Finland .................................. 872051

[51] Int. Cl.⁵ .............................................. A61K 9/16
[52] U.S. Cl. .................................... 424/494; 424/497; 424/498
[58] Field of Search ................. 424/490, 497, 498, 494

[56] References Cited

U.S. PATENT DOCUMENTS

| 2,828,206 | 3/1958 | Rosenberg | 424/498 |
| 2,921,883 | 1/1960 | Reese et al. | 424/498 X |
| 2,963,402 | 12/1960 | Nalin et al. | 424/498 X |
| 3,080,294 | 3/1963 | Shepard | 424/498 |
| 3,119,742 | 1/1964 | Heimlich et al. | 424/498 |
| 3,256,153 | 6/1966 | Heimlich | 424/498 X |
| 3,432,593 | 3/1969 | Shepard | 424/498 |
| 4,460,563 | 7/1984 | Calanchi | 424/498 |
| 4,650,665 | 3/1987 | Kronenthal et al. | 424/435 |

FOREIGN PATENT DOCUMENTS 0821790  10/1959  United Kingdom ................ 424/498

Primary Examiner—Thurman K. Page
Attorney, Agent, or Firm—Burns, Doane, Swecker & Mathis

[57] ABSTRACT

The invention relates to a new composition for use on a pharmaceutical granule. The composition is three-layered, comprising as the innermost layer a substantially pure fat, as the middle layer a mixture of fat and polymer, and as the outermost layer again a substantially pure fat.

The composition according to the invention produces a preparation which is tasteless, especially when administered in the form of a powder or a mixture, even if the phrmaceutical to be dosed has a bad taste. Also, the preparation keeps well in mixture, and it enables a pharmaceutical to be transported past the stomach for release/absorption at the beginning of the small intestine.

12 Claims, 2 Drawing Sheets

COMPOSITION FOR THE ORAL ADMINISTRATION OF PHARMACEUTICALS

The present invention relates to a new composition by means of which pharmaceuticals can be administered in powder form, in capsules or, particularly, in liquid form. The last-mentioned form for administering pharmaceuticals is known as a mixture, which means that the pharmaceutical has been mixed with a liquid carrier. The question is in particularly important for poorly soluble pharmaceuticals.

One objective in the preparation of pharmaceuticals has long been to produce a pharmaceutical composition which has no side effects and from which the pharmaceutical is absorbed as completely as possible at the desired point of the alimentary canal, for example at the beginning of the small intestine. In many cases it is important that a pharmaceutical can be transported past the stomach since the gastric juice may convert the pharmaceutical into a less active or even inactive form. Thus the absorption should not take place before the small intestine.

The cases in which a pharmaceutical is administered in the form of a mixture constitute a field of their own. In addition to the above factors, in this case it is also necessary to take into account the effects exerted on the pharmaceutical by the carrier liquid of the mixture. The mixture is virtually the only form for administering pharmaceuticals in certain special cases such as small children and old individuals, and people whose ability to swallow is for one reason or another impaired. In such cases it is not possible to administer tablets or capsules. The breaking of a tablet or a capsule for its part often means that its desired properties are eliminated. Especially when children are concerned the form in which a pharmaceutical is administered should be tasteless or preferably have a good taste.

With certain pharmaceuticals, attempts have been made specifically to avoid the bad taste by preparing the pharmaceutical as a salt or ester which no longer has a bad taste. This had, however, resulted in two disadvantages. One is that the bad taste has, nevertheless, not been totally eliminated, since the dosage form containing the reaction product still contains also some amount of the bad-tasting initial component, and the other is that the absorbability has crucially decreased. In one known mixture of this type, erythromycin ethyl succinate has been used as the active compuond.

Attempts have been made to satisfy in highly different ways the needs prevailing in the field, and thus it is known to coat a tablet with one or several layers of a substance which, it is hoped, has the desired properties. Hundreds of such compositions are known. In many compositions, various plastic materials have been used as the coating, either alone or together with plastics of other types. Certain cellulose derivatives and fats have also been used.

When the question is of a mixture, the state of the art is much more restricted than that of tablets, which indicates that the preparation of a mixture is an art which requires especially great knowhow.

EP application 148811 discloses a composition by means of which, it is claimed, it is possible to transport a pharmaceutical highly soluble in acid conditions, for example in the stomach, past the stomach into the small intestine, where it is absorbed into the blood circulation. In this composition, a double layer of coating is used on a granule of the pharmaceutical, the inner coating being, according to the examples given, a mixture of ethyl cellulose and Eudragit RL plastic and the outer one for its part being a cellulose derivative. The obtained pharmaceutical composition has thereafter been packed into capsules.

In the above-mentioned patent there is no mention regarding whether the composition is usable in mixtures, but it can be clearly determined from the layers used that the composition would not remain sufficiently long in mixture in order to be capable of being used in a mixture. It can further be mentioned that the diffusion membrane used in the composition is intended specifically for producing a retarding effect, and the pharmaceutical would give taste with the mixture. The release of the pharmaceutical would be continuously retarded and not be targeted only at a suitable point of absorption as is necessary, for example, in the use of erythromycins.

Another alternative in accordance with the state of the art is disclosed in EP Patent Application No. 169236, which describes a composition intended specifically for use in a mixture and which is claimed to remain in mixture for at least 35 days. In this alternative, also, two layers are used, of which the inner one is made up of fat, wax, fatty acid, fatty alcohol or ester, having a melting point at maximum 120° F., and the outer layer for its part is made up of prolamine, cellulose derivative, cellulose ether or starch.

The above-mentioned composition contains as the first coating layer a substance which decomposes into a permeable form in the alimentary canal, which is a principle foreign to the composition now invented. In addition, the EP publication aims at a so-called controlled release composition, whereas in the present composition the purpose is to transport the pharmaceutical to a certain point in the alimentary canal, without a release-retarding effect.

The object of the present invention is to provide a composition by means of which the disadvantages of the state of the art can be eliminated and a composition is produced which can be used for oral administration in powder form, packed in capsules or, specifically, in mixture form, for example, mixed with seasoned sugar syrups of pharmacopeias and which composition transports the pharmaceutical past the stomach without the gastric juices being able to affect the pharmaceutical. In addition, the composition according to the invention causes an almost complete absorption of the pharmaceutical specifically at the beginning of the small intestine. The purpose is also to avoid substantially completely the disadvantages of administering bad-tasting pharmaceuticals, especially to children.

Figure 1:
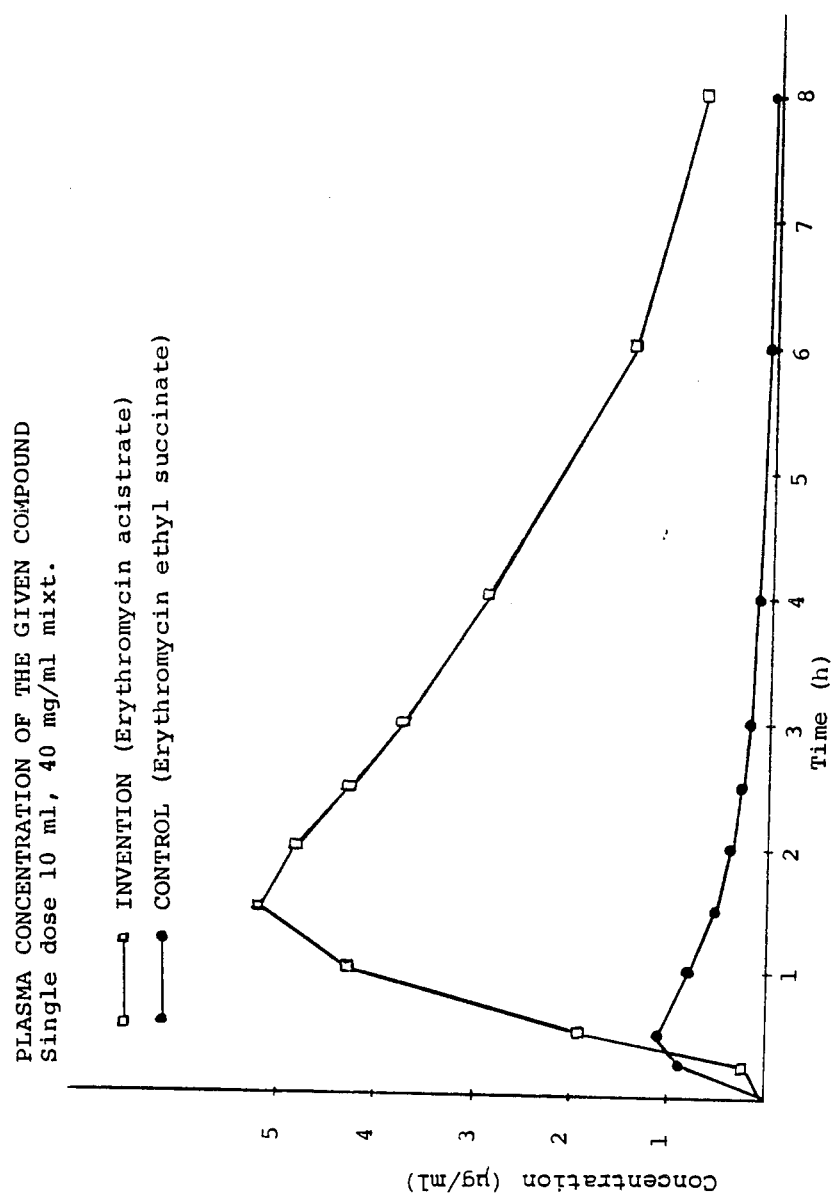
FIG. 1 is a graph showing the plasma concentration of erythromycin acistrate, a compound of the present invention, and the plasma concentration of a control.

The advantages of the composition according to the invention have been achieved by using, on top of the pharmaceutical core, three layers, of which the first is made up of a fat described later in greater detail. The second layer is made up of a mixture of the above-mentioned fat and a polymer described later in greater detail, and the outer-most layer for its part is made up of the substantially pure fat which was used in the first layer. On the interfaces the fat and the polymer may be somewhat mixed with one another. The above-mentioned fat may already have been used for combining small particles of the pharmaceutical into larger granules, pellets. The median of the size distribution of the fatty pellets produced according to the invention and containing the pharmaceutical inside them is usually about 30–200 μm, suitable about 50–150 μm, and preferably 80–140 μm.

Thus is produced a composition which is tasteless, which lasts in mixture unchanged for long periods, which decomposes and breaks up at the beginning of the small intestine and which, in addition to everything else, yields complete release and absorption even for poorly absorbable pharmaceuticals.

According to the invention, fats suitable for use as the above-mentioned fats include specifically the triglycerides of saturated large-molecule fatty acids having 11–23, specifically 12–18, carbon atoms. Also suitable for the purpose are mixtures of the triglycerides of the above-mentioned fatty acids. The triglyceride of myristic acid, glyceryl trimyristrate, is especially suitable for the use according to the invention. The melting points of the triglyerides presented are above 47° C., especially above 50° C.

Any ester of phthalic acid and a cellulose derivative, such as hydroxypropl methyl cellulose phthalate, soluble in water at pH exceeding 4.5, is suitable for use as the polymer in accordance with the invention.

By means of the composition according to the invention it is possible to produce a mixture which keeps well, since the protective layer used is completely insoluble in water. On the other hand, the composition according to the invention travels through the stomach in a substantially unchanged form, since the acids and enzymes present in the stomach do not decompose the coating according to the invention, and pH as such has no effect on dissolving of the coating. Thus decomposition does not start before the beginning of the small intestine, where the pharmaceutical is released rapidly and absorbed into the circulation. A product coated with the coating according to the invention can thus also be used for local treatment in the intestinal area.

The total amount of the coating materials used is 50–95% by weight of the weight of the completed product. In the layer in which both fat and polymer are used, the proportion of polymer in the layer is 15–99% by weight.

In compositions according to the invention it is possible to dose any poorly soluble pharmaceutical, but those substances having properties for which the above-described dosage form would be especially desirable include various antibiotics such as erythromycin and its derivatives, penicillins and penicillin derivatives, and also other antibiotics. Some examples of antibiotics for the administration of which the composition under discussion is especially suitable include erythromycin acistrate, other erythromycins such as erythromycin base and erythromycin stearate, phenoxymethyl penicillin, ampicillin and certain cefalosporins, chemotherapeutic substances such as sulfonamides, tetracyclines, trimethoprim, nitrofurantoin, etc.

The composition according to the invention is prepared by using the so-called fluidized-bed technique, according to which the fat, dissolved in a solvent, is deposited on the surface of a pharmaceutical granule which has been previously pelleted by using a fat of the same group, and on the pellet thus obtained there are further deposited, also from a solvent, a layer of a mixture of fat and polymer, and on the outer surface again pure fat. The resulting pulverulent substance is packed for oral administering either as such as a powder or in capsules, or the powder is used for the preparation of a mixture. Conventionally a mixture is prepared by mixing a suitable amount of the powder according to the invention with flavored syrup solutions.

Solvents suitable for the method specifically include halogenated hydrocarbons such as methylene chloride, acetone, a lower alcohol, or a mixture of these. Technically the coating is produced by suspending the particles to be coated at a given time in a suitable apparatus and by spraying the coating material, dissolved in solvents, into the powder. The solvent evaporates and the coating material remains on the granule. This procedure is repeated with the desired materials for the desired number of times in order to produce the various layers.

The properties of the composition according to the invention were tested using the following experiments.

The properties of the invention were examined by performing absorption experiments in connection with which volunteer patients ingested mixture products provided with the coating according to the invention. Each of the test subjects found the mixture good tasting, and no feeling of the bad taste of the pharmaceutical was reported.

Figure 2:
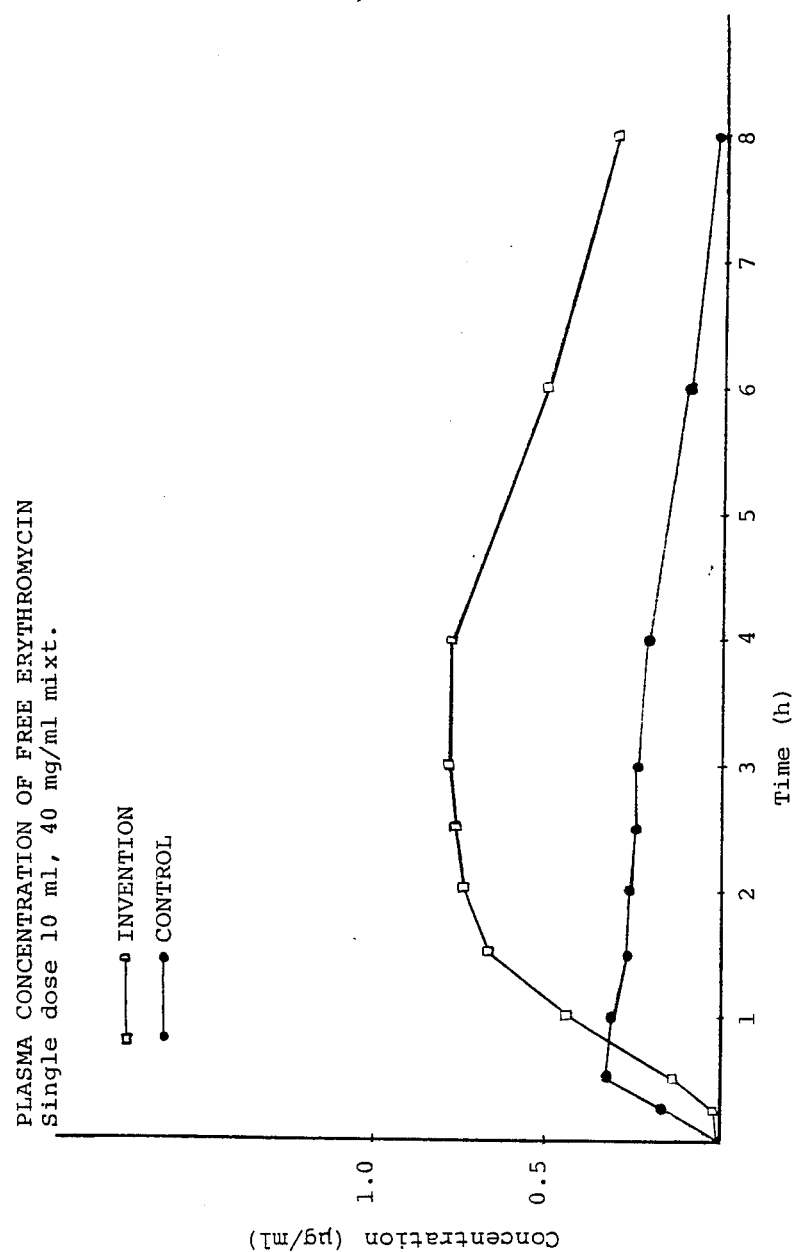
FIG. 2 is a graph showing the plasma concentration of free erythromycin for the compound of the present invention and a control.

In the absorption test the erythromycin acistrate mixture provided with a coating according to the invention was compared with the erythromycin ethyl succinate mixture which is on the market and which is currently used worldwide for erythromycin treatment in pediatric practice. The results of the absorption tests are illustrated in accompanying FIGS. 1-2, which clearly show that the effective proportion of the mixture preparation according to the invention is crucially better than that of the reference preparation, as regards both the unhydrolyzed esters and free erythromycin. In the figures, the AUC value (AUC=Area Under Curve) of the unhydrolyzed ester is 23.01 for the composition according to the invention and 2.04 for the reference preparation, and the respective values of free erythromycin are 5.95 for the preparation according to the invention and 1.48(μg/ml )×h for the reference preparation.

In the cases of a large proportion of antibiotics the duration of a treatment course is approximately ten days. For this reason it is a requirement that mixtures should keep substantially unchanged for at least 14 days. It was noted that the erythromycin acistrate mixture provided with the coating according to the invention remained substantially unchanged for the above-mentioned period.

As can be seen unambiguously from the above experiments, the composition according to the invention was extremely successful with respect to all of the desired properties. It keeps well, is tasteless and is absorbed well.

The following examples illustrate the process for preparing preparations equipped with the coating according to the invention.

EXAMPLE 1

A coated powder of erythromycin acistrate

| | |
|---|---|
| Erythromycin acistrate | 65 mg |
| L | |

|  |  |
|---|---|
| glyceryl trimyristate | 60 mg |
| * methylene chloride | 180 mg |
| II |  |
| glyceryl trimyristate | 20 mg |
| HPMCP | 20 mg |
| * concentrated alcohol | 60 mg |
| * methylene chloride | 230 mg |
| III |  |
| glyceryl trimyristate | 60 mg |
| * methylene chloride | 180 mg |

* is evaporated during the process

Small fatty pellets (size distribution median 100 μm) were prepared by the fluidized-bed technique by granulating and partly coating the pharmaceutical first with solution I. Next a fat-polymer layer from solution II was deposited on the particle surfaces and finally a pure fat from solution III.

By using the method described in Example 1, the following coatings were also prepared for various pharmaceuticals.

EXAMPLE 2

Coated powder of erythromycin acistrate

|  |  |
|---|---|
| Erythromycin acistrate | 65 mg |
| I |  |
| glyceryl trimyristate | 40 mg |
| * methylene chloride | 160 mg |
| II |  |
| glyceryl trimyristate | 10 mg |
| HPMCP | 10 mg |
| * concentrated alcohol | 30 mg |
| * methylene chloride | 115 mg |
| III |  |
| glyceryl trimyristate | 10 mg |
| * methylene chloride | 30 mg |

* is evaporated during the process

EXAMPLE 3

A coated powder of erythromycin acistrate

|  |  |
|---|---|
| Erythromycin acistrate | 65 mg |
| I |  |
| glyceryl trimyristate | 90 mg |
| * methylene chloride | 270 mg |
| II |  |
| glyceryl trimyristate | 40 mg |
| HPMCP | 40 mg |
| * methylene chloride | 250 mg |
| III |  |
| glyceryl trimyristate | 100 mg |
| * methylene chloride | 300 mg |

* is evaporated during the process

EXAMPLE 4

A coated powder of erythromycin acistrate

|  |  |
|---|---|
| Erythromycin acistrate | 65 mg |
| I |  |
| glyceryl trimyristate | 60 mg |
| * methylene chloride | 180 mg |
| II |  |
| glyceryl trimyristate | 10 mg |
| HPMCP | 50 mg |
| * methylene chloride | 250 mg |
| III |  |
| glyceryl trimyristate | 60 mg |
| * methylene chloride | 180 mg |

* is evaporated during the process

EXAMPLE 5

A coated powder of erythromycin base

|  |  |
|---|---|
| Erythromycin | 45 mg |
| I |  |
| glyceryl trimyristate | 60 mg |
| * methylene chloride | 180 mg |
| II |  |
| glyceryl trimyristate | 20 mg |
| HPMCP | 20 mg |
| * concentrated alcohol | 60 mg |
| * methylene chloride | 230 mg |
| III |  |
| glyceryl trimyristate | 60 mg |
| * methylene chloride | 180 mg |

* is evaporated during the process

EXAMPLE 6

A coated powder of erythromycin stearate

|  |  |
|---|---|
| Erythromycin stearate | 65 mg |
| I |  |
| glyceryl trimyristate | 60 mg |
| * methylene chloride | 180 mg |
| II |  |
| glyceryl trimyristate | 20 mg |
| HPMCP | 20 mg |
| * concentrated alcohol | 60 mg |
| * methylene chloride | 230 mg |
| III |  |
| glyceryl trimyristate | 60 mg |
| * methylene chloride | 180 mg |

* is evaporated during the process

EXAMPLE 7

A coated powder of erythromycin acistrate

|  |  |
|---|---|
| Erythromycin acistrate | 65 mg |
| I |  |
| glyceryl trilaurate | 60 mg |
| * methylene chloride | 180 mg |
| II |  |
| glyceryl trilaurate | 20 mg |
| HPMCP | 20 mg |
| * concentrated alcohol | 60 mg |
| * methylene chloride | 230 mg |
| III |  |
| glyceryl trilaurate | 60 mg |
| * methylene chloride | 180 mg |

* is evaporated during the process

EXAMPLE 8

A coated powder of erythromycin acistrate

|  |  |
|---|---|
| Erythromycin acistrate | 65 mg |
| I |  |
| capric acid triglyceride | 60 mg |
| * methylene chloride | 180 mg |
| II |  |
| capric acid triglyceride | 20 mg |
| HPMCP | 20 mg |

| | |
|---|---|
| -continued | |
| * concentrated alcohol | 60 mg |
| * methylene chloride | 230 mg |
| III | |
| capric acid triglyceride | 60 mg |
| * methylene chloride | 180 mg |

* is evaporated during the process

EXAMPLE 9

A coated powder of erythromycin acistrate

| | |
|---|---|
| Erythromycin acistrate | 65 mg |
| I | |
| stearic acid triglyceride | 60 mg |
| * methylene chloride | 180 mg |
| II | |
| stearic acid triglyceride | 20 mg |
| HPMCP | 20 mg |
| * methylene chloride | 250 mg |
| III | |
| stearic acid triglyceride | 60 mg |
| * methylene chloride | 180 mg |

* is evaporated during the process

EXAMPLE 10

A coated powder of erythromycin acistrate

| | |
|---|---|
| Erythromycin acistrate | 65 mg |
| I | |
| lignoceric acid triglyceride | 60 mg |
| * methylene chloride | 180 mg |
| II | |
| lignoceric acid triglyceride | 20 mg |
| HPMCP | 20 mg |
| * methylene chloride | 250 mg |
| III | |
| lignoseric acid triglyceride | 60 mg |
| * methylene chloride | 180 mg |

* is evaporated during the process

EXAMPLE 11

A coated powder of phenoxymethyl penicillin

| | |
|---|---|
| Phenoxymethyl penicillin | 100 000 IU |
| I | |
| glyceryl trimyristate | 60 mg |
| * methylene chloride | 180 mg |
| II | |
| glyceryl trimyristate | 20 mg |
| HPMCP | 20 mg |
| * methylene chloride | 250 mg |
| III | |
| glyceryl trimyristate | 60 mg |
| * methylene chloride | 180 mg |

* is evaporated during the process

EXAMPLE 12

A coated powder of sulfasalazine

| | |
|---|---|
| Sulfasalazine | 60 mg |
| I | |
| glyceryl trimyristate | 60 mg |
| * methylene chloride | 180 mg |
| II | |
| glyceryl trimyristate | 20 mg |
| HPMCP | 20 mg |

| | |
|---|---|
| -continued | |
| * methylene chloride | 250 mg |
| III | |
| glyceryl trimyristate | 60 mg |
| * methylene chloride | 180 mg |

* is evaporated during the process

EXAMPLE 13

A coated powder of sulfasalazine

| | |
|---|---|
| Sulfasalazine | 60 mg |
| I | |
| glyceryl tristearate | 60 mg |
| * methylene chloride | 180 mg |
| II | |
| glyceryl tristearate | 20 mg |
| cellulose-acetate phthalate | 20 mg |
| * acetone | 60 mg |
| * methylene chloride | 230 mg |
| III | |
| glyceryl tristearate | 60 mg |
| * methylene chloride | 180 mg |

* is evaporated during the process

EXAMPLE 14

A coated powder of erythromycin acistrate

| | |
|---|---|
| Erythromycin acistrate | 65 mg |
| I | |
| glyceryl trimyristate | 60 mg |
| * methylene chloride | 180 mg |
| II | |
| glyceryl trimyristate | 3 mg |
| HPMCP | 37 mg |
| * concentrated alcohol | 60 mg |
| * methylene chloride | 230 mg |
| III | |
| glyceryl trimyristate | 60 mg |
| * methylene chloride | 180 mg |

* is evaporated during the process

We claim:

1. A pharmaceutical composition of matter for the oral administration of pharmaceuticals, said composition comprising a pharmaceutical core having present thereon a first layer, a second layer and a third layer, said first layer comprising substantially pure fat, said second layer comprising a mixture of substantially pure fat and polymer, and said third layer comprising substantially pure fat, said pharmaceutical composition being designed to substantially decompose at the beginning of the small intestine, wherein said fat is a triglyceride of one or more saturated fatty acids having 11 to 23 carbon atoms and said polymer is an ester of phthalic acid and a cellulose derivative that is soluble in water at a pH of 4.5 or greater.

2. The pharmaceutical composition according to claim 1 wherein said fatty acid triglyceride is a triglyceride of a saturated fatty acid containing 12 to 18 carbon atoms.

3. The pharmaceutical composition according to claim 1 wherein said substantially pure fat is glyceryl trimyristate.

4. The pharmaceutical composition according to claim 1 wherein said ester comprises hydroxypropyl methyl cellulose phthalate.

5. The pharmaceutical composition according to claim 1, wherein said first, second and third layers combined comprise 50 to 95% by weight of the entire pharmaceutical composition of matter.

6. The pharmaceutical composition of matter according to claim 1 wherein said polymer in the second layer comprises 15 to 99% by weight of the second layer.

7. The pharmaceutical composition according to claim 1 wherein the median size distribution of the pharmaceutical core, the first layer, the second layer and the third layer combined is about 30 to 200 μm.

8. The pharmaceutical composition according to claim 7 wherein the median size distribution is about 50 to 150 μm.

9. The pharmaceutical composition according to claim 8 wherein the median size distribution is 80 to 140 μm.

10. A process for the preparation of a pharmaceutical composition of matter for the oral administration of pharmaceuticals, said process comprising
(a) pelleting a pharmaceutical granule;
(b) dissolving a substantially pure fat in a solvent and depositing said dissolved fat as a first layer on the surface of the pharmaceutical pellet;
(c) dissolving a mixture of a substantially pure fat and polymer in a solvent and depositing same as a second layer on said pharmaceutical pellet containing said first layer; and
(d) dissolving a substantially pure fat in a solvent and depositing said dissolved fat as a third layer on the surface of the pharmaceutical pellet containing said first and second layers,
wherein said fat is a triglyceride of one or more saturated fatty acids having 11 to 23 carbon atoms and said polymer is an ester of phthalic acid and a cellulose derivative that is soluble in water at a pH of 4.5 or greater.

11. The method according to claim 10 wherein said solvent is a halogenated hydrocarbon, acetone, a lower alcohol or mixture thereof.

12. The method according to claim 11 wherein said halogenated hydrocarbon is methylene chloride.

* * * * *